United States Patent
Cotton et al.

(10) Patent No.: US 8,145,294 B2
(45) Date of Patent: Mar. 27, 2012

(54) METHOD AND APPARATUS FOR QUANTIFYING TISSUE HISTOLOGY

(75) Inventors: Symon D'Oyly Cotton, Great Gransden (GB); Stephen John Preece, Cheadle Hulme (GB); Elzbieta Claridge, Birmingham (GB)

(73) Assignee: Medx Health Corporation, Mississauga, Ontario (CA)

( * ) Notice: Subject to any disclaimer, the term of this patent is extended or adjusted under 35 U.S.C. 154(b) by 1742 days.

(21) Appl. No.: 10/523,158

(22) PCT Filed: Jul. 30, 2003

(86) PCT No.: PCT/GB03/03367
§ 371 (c)(1),
(2), (4) Date: Oct. 13, 2005

(87) PCT Pub. No.: WO2004/010862
PCT Pub. Date: Feb. 5, 2004

(65) Prior Publication Data
US 2006/0276966 A1   Dec. 7, 2006

(30) Foreign Application Priority Data
Jul. 30, 2002 (GB) ................... 0217570.1

(51) Int. Cl.
*A61B 6/00* (2006.01)
(52) U.S. Cl. ......... 600/476; 600/473; 600/475; 600/477
(58) Field of Classification Search .............. 600/473, 600/475–476
See application file for complete search history.

(56) References Cited

U.S. PATENT DOCUMENTS

| 4,114,604 | A | | 9/1978 | Shaw et al. |
| 5,640,957 | A | * | 6/1997 | Kaminski et al. ............ 600/407 |
| 5,974,338 | A | * | 10/1999 | Asano et al. ................ 600/323 |
| 6,289,236 | B1 | * | 9/2001 | Koenig et al. ............... 600/477 |
| 6,681,128 | B2 | * | 1/2004 | Steuer et al. ................ 600/322 |
| 6,775,565 | B1 | * | 8/2004 | Wieringa .................... 600/322 |
| 7,054,674 | B2 | * | 5/2006 | Cane et al. .................. 600/407 |
| 2001/0037058 | A1 | | 11/2001 | Stone |

(Continued)

FOREIGN PATENT DOCUMENTS

JP     61-011096     4/1986
(Continued)

OTHER PUBLICATIONS

Maloney & Wendell, "Color constancy: a method for recovering surface spectral reflections", J. Opt. Soc. Am. A 3, 29-33 (1986).

(Continued)

*Primary Examiner* — Long V. Le
*Assistant Examiner* — Katherine Fernandez
(74) *Attorney, Agent, or Firm* — Tracy Jong Law Firm; Tracy P. Jong

(57) ABSTRACT

Method of analysing at least one parameter of a body component is provided. The method includes illuminating the component or body with light of at least a first and second waveband, receiving light of at least said first and second wavebands remitted by the component at a photoreceptor or photoreceptors, and analysing the light received at the photoreceptor(s) to provide a ratio between the amount of light remitted of the first waveband and the amount of light remitted of the second waveband, and from this calculating the component parameter.

19 Claims, 9 Drawing Sheets

U.S. PATENT DOCUMENTS

| | | |
|---|---|---|
| 2001/0056237 A1 | 12/2001 | Cane et al. |
| 2002/0056237 A1 | 5/2002 | Price |

FOREIGN PATENT DOCUMENTS

| | | |
|---|---|---|
| JP | 2005-161609 | 6/2005 |
| WO | WO 98/22023 | 5/1998 |
| WO | WO 00/75637 A1 | 12/2000 |
| WO | WO 02/02001 A2 | 1/2002 |

OTHER PUBLICATIONS

G. Healey, "Using colour for geometry-insensitive segmentation"' J. Opt. Soc. Am. A 6, 920-937 (1989).

M. A. Afromowitz, G.S. Van Liew & D.M. Heimbach, "Clinical evaluation of burn injuries using an optical reflectance technique", IEEE trans. Biomed. Eng. BME-34, 114-127 (1987).

Afromowitz, Desoto & Norton, "Multispectral imaging of burn wounds: a new clinical instrument for evaluating burn depth", IEEE trans. Biomed. Eng. 35, 842-849 (1988).

S. Shafer, "Using color to separate reflection components", Color Res. Appl. 4, 210-218 (1985).

MM Lipschutz, Differential Geometry (McGraw-Hill Book Company, New York, 1969).

T. Back and H.P. Schwefel, "An overview of evolutionary algorithms for parameter optimization", Evolutionary Computation 1, 1-23, (1993).

L. Davis, The handbook of genetic algorithms (Van Nostrand Reingold, New York, 1991.

D. Goldberg, Genetic algorithms in search, optimization and machine learning (Addison-Wesley, London 1989).

S.D. Cotton and E. Claridge, "Developing a predictive model of human skin coloring", Proc. of SPIE Med. Imag. 2708, 814-825 (1996).

P. Kubelka and F. Munk, "Ein Beitrag zur Optik der Farbanstriche", "Z Tech. Opt" 11, 593-611 (1931).

Anselmo, VJ et al., "Multispectral Photographic Analysis. A New Quantitative Tool to Assist in the Early Diagnosis of Thermal Burn Dept", Annals of Biomedical Engineering vol. 5, No. 2, Jun. 1977, pp. 179-193.

Shashua, Amnon et al. "The Quotient Image: Class-Based Re-Rendering and Recognition with Varying Illuminations", IEEE Transactions on Pattern Analysis and Machine Intelligence, vol. 23, No. 2, Feb. 2001, pp. 129-139.

\* cited by examiner

METHOD AND APPARATUS FOR QUANTIFYING TISSUE HISTOLOGY

This application claims priority to International Patent Application No. PCT/GB03/003367 filed on Jul. 30, 2003, which claims priority to GB Patent Application No. 0217570.1 filed on Jul. 30, 2002.

This invention relates to a method and apparatus for quantifying tissue histology. In particular the invention relates to methods using an analysis of the spectra of remitted light to establish information on the properties of the tissue. The invention is also applicable to methods and apparatus which rely upon a spectral analysis of light remitted, emitted, and/or transmitted from any material or object under test where they have parameters exhibiting wavelength specific optical effects.

There exists the need for a system, which can recover histological parameters from biological tissue in a way which is invariant to the intensity of the incident illumination and scene geometry. It is an objective of the present invention to provide such a technique. Such a system would be of value in systems where the topology of the tissue or image surface in not known a priori. It would also be of value in a system where the intensity of the illuminating light cannot be assumed constant. Potential applications include but are not limited to imaging and analysis of the tissue of the gastrointestinal track with an endoscope and imaging and analysis of skin over areas where there is a significant change in curvature, such as the face.

A system is currently in existence, which is able to assist clinicians in their diagnosis of melanoma. The technique is based on a patent, international patent application publication number WO98/22023. This system is based on the discovery that when the range of colouration of normal human skin is plotted in a standard RGB colour space, it lies on a well-defined surface. Furthermore, if an abnormality such as dermal melanin is present, the colouration of the skin changes in such a way as to move points away from the surface which describes healthy skin. By incorporating a calibration calculation which allows variation of dermal thickness to be taken into account, the technique is able to detect abnormalities and thus assist clinicians in their diagnosis of melanoma.

The fundamental principle behind this system is that it is possible to construct a mathematical function that relates image values, measured using a digital camera, to appropriate histological parameters. Using this functional relation, it is possible to obtain the value of each parameter at every point across a given image. A parametric map can then be produced which gives a grey-scale representation of the parameter value across the whole image.

Although this system has been proved to be clinically effective, it requires exact calibration of the illuminating light source and does not take into account any variation in surface geometry. Thus the technique is limited to problems where a probe can be placed in contact with the region of interest. This ensures that the incident light is controlled and calibrated and that it's angle of incidence remains constant.

The proposed invention relates to a method for imaging tissue in such a way to give quantitative spectral data independently of the surface geometry or the intensity of the illuminating light. This will allow a non-contact form of imaging and analysis which will be applicable to many different applications. The method may be used with the technique described in W098/22023 and subsequent related patents but is not exclusive to it.

The method concentrates upon the analysis of light remitted by the tissue, in the illuminating light which penetrates the tissue to some depth and is reflected (or scattered or/and absorbed) to different degrees at different depths due to different parameters of the tissue. Effects due to surface reflection are to be eliminated from the analysis.

Substantial work has been carried out to develop image analysis algorithms which are able to identify different objects irrespective of the illuminating light. Many of the techniques developed are based around the linear model of surface reflectance as proposed in L Maloney and B. Wandell, "Color constancy: a method for recovering surface spectral reflectance", J. Opt. Soc. Am. A 3, 29-33 (1986). This approach is based on the idea that the surface reflectance of any object within an imaged scene can be expressed as a weighted sum of basis spectral reflectance functions:

$$S(\lambda) = \sum_{j=1}^{n} \sigma_j S_j(\lambda) \qquad (1)$$

and that the illuminating light can similarly be expressed as a weighted sum of basis lights. It has been shown that only a small number of basis functions are required to obtain accurate approximations to the surface reflectances of many naturally occurring objects and also the spectral variation of natural daylight.

With this technique it is possible to recover the vector of weighting constants $\sigma_j$ from a vector of image values and thus specify the spectral reflectance of the imaged object at every pixel. Every potential imaged object object characteristic will have a unique spectral reflectance. Thus, if the spectral reflectance can be determined using a linear model, then the parameter vector can be specified. With this approach it should be possible to recover a parameter vector from the vector of image values at each pixel. Unfortunately the method is only able to recover the weighting constants $\sigma_j$ to within a multiplicative scaling factor and thus cannot be used to specify the exact spectral reflectance and therefore the exact parameter vector.

An approach to geometry-insensitive segmentation of images has been developed in G. Healey, "Using colour for geometry-insensitive segmentation," J. Opt. Soc. Am. A 6, 920-937 (1989), and is based on the idea of normalised colour. With this approach image values are first divided by an estimate of normalised colour. This estimate is based on approximating the incoming signal from colour pixel values by using a finite-dimensional linear approximation to represent the colour signal.

Using these normalised values, different metal and dielectric materials can be identified across an imaged scene in which the geometry varies considerably.

A similar technique has been applied to evaluate burn injuries {M. A. Afromowitz, G. S. van Liew and D. M. Heimbach, "Clinical evaluation of burn injuries using an optical reflectance technique", IEEE trans. Biomed. Eng. BME-34, 114-127 (1987), and M. A. Afromowitz, J. B. Callis D. M. Heimbach, L. A. Desoto and M. K. Norton, "Mulitspectral imaging of burn wounds: a new clinical instrument for evaluating burn depth", IEEE tran. Biomed. Eng. 35, 842-849 (1988)}. In this case, RGB image values were normalised by dividing them by the response of an IR filter. From the normalised values it was possible to assess the extent of burn damage across a given area of imaged skin.

There exists a need for a non-invasive technique for analysing an object or material (which may be complex, for example multi-component and/or multi-layer and which may be solid, gaseous, liquid, etc) which does not require calibration to take into account changing illumination conditions.

SUMMARY OF THE INVENTIONS

According to a first aspect of the invention there is provided a method of analyzing at least one parameter of a body component, comprising the steps of illuminating the component with light of at least a first and second waveband, receiving light of at least said first and second wavebands remitted by the component at a photoreceptor, and analyzing the light received at the photoreceptor to provide a ratio between the amount of light remitted of the first waveband and the amount of light remitted of the second waveband, and from this calculating the component parameter.

Thus the invention lies in the appreciation that by skillful selection of the wavebands of light remitted by a biological component, usually human or animal tissue, the ratio between two such wavebands can be used to create a useful parametric image of the biological component. The wavebands may be calculated using a biological or mathematical model to monitor the relationship between a particular image ratio and the parameter to create a function which then can be used for monitoring that parameter in the biological component. As an alternative to creating a function the measured waveband ratios can be compared with the predictions of a model either mathematical or experimentially measured.

According to a second aspect of the invention, there is provided a method of analyzing at least one parameter of a body component, comprising the steps of illuminating the component with light of at least a first and second predetermined waveband, receiving light of at least said first and second predetermined wavebands remitted by the component reflected by the surface at a photoreceptor but eliminating light reflected by the surface of the component, where the predetermined wavebands are chosen such that the component parameter is a one to one function of the ratio between the amount of light remitted by the component of the first predetermined wavebands and the amount of light remitted by the component of the second predetermined waveband, and analyzing the light received at the photoreceptor to provide a ratio between the light of the first waveband and the light of the second waveband, and from this calculating the component parameter.

The method is such that the effects of reflection rather than remittance will be ignored. Although this would appear to limit the application to components which do not have a specular component of reflection, such as many organic objects, image processing algorithms have been developed to allow removal of this component of reflection giving greater applicability of the technique. For example, it has been shown that it is possible to remove the highlights from complex images containing inhomogeneous dielectrics. It is also possible to remove the surface component of reflection using a polarising filter. Once this component has been removed from image data, it will be possible to use the techniques described here.

Preferably the effects of surface reflection are eliminated by providing a pair of cross-polarised linear polarizing filters. The first of these is placed in front of the source of illumination and the second in front of the image capture system. There are however other methods which will be apparent the skilled reader which could be used to eliminate surface reflection effects.

The body component may be any biological component but is most usefully animal tissue.

Each waveband referred to may comprise a single wavelength, but in practice will preferably comprise a band of wavelengths, detectable by the photoreceptor.

The light emitted by the light source may be a white light or light of a plurality of wavelengths, some of which are outside the predetermined wavebands, and filters may be used to limit the light received by the photoreceptor to the desired wavebands. Such filters may be placed between the light source and the tissue, between the tissue and the photoreceptor or at both positions. Alternatively white light may be emitted by the light source and received by the photoreceptor with the analysis means establishing the amount of light within the desired waveband.

To understand why this process eliminates any variation in illumination intensity and surface geometry it is necessary to consider the dichromatic reflection model. This was first proposed by S. Shafer in "Using colour to separate reflection components" Color. Res. Appl. 4, 210-218 (1985) and states that light remitted from an object is the sum of two components, the "body" component and the "surface" component. The body component refers to physical processes occurring after penetration of light into the material and the surface term to reflections which take place at the surface of the object. The body component is a function of the spectral characteristics of the object, whereas the surface component depends only on the object geometry and the incident light. The theory states further that each component can be considered the product of a geometrical term and a wavelength dependent term.

The proposed invention is used where an optical system makes spectral measures of tissue. One embodiment of such an optical system uses a colour digital camera as the photoreceptor, although a monochrome digital camera arranged to take sequential images with different coloured light sources could also be used. Both these embodiments may have millions of image pixels or very few pixels, or even just one pixel in the case of the monochrome system. The optical system may work in the visual spectrum, or over an extended spectrum to include non visible wavelengths. These non visible wavelengths may include infra-red light. This infra-red light may include wavelengths in the 600 nm to 800 nm band.

In the case of a conventional colour digital camera, the system measures light through a number of optical filters. Image values for a specific image location, corresponding to the nth filter, are given by $$i^n = K_b C_b^n + K_s C_s^n$$

where $K_b$ and $K_s$ are the geometric terms of the body and surface component respectively and $C_b$ and $C_s$ are colour terms. By using the system of polarising filters described above it is possible to eliminate surface reflection. Image values are then given as a simple product of a geometric term and a colour, or wavelength dependent term. The illuminating light is now written as $$E(\lambda) = \epsilon_0 E_0(\lambda)$$

where $\epsilon_0$ is a wavelength independent scaling factor determined by the intensity of the light source but which does not change, or changes in a known manner, will wavelength. This allows the dichromatic reflection model to be written as $$i^n = \epsilon \int E_0(\lambda) S(\lambda) R^n(\lambda) d\lambda$$

where $\epsilon = \epsilon_0 K_b$. The function $R^n(\lambda)$ defines the spectral response of the nth filter and $S^n(\lambda)$ the remitted spectrum of the illuminated tissue. It is essential that both $E_0(\lambda)$ and $R^n(\lambda)$ are known for the given imaging system. Thus the invention is preferentially utilised in to systems where tissue of interest is illuminated with light of know spectral characteristics.

If the optical system records a M-dimensional vector of image values at each pixel then it is possible to define a N-dimensional vector of image ratios, which is obtained by defining appropriate ratios of image values. An example of such a vector is $$r = \left(\frac{i_2}{i_1}, \frac{i_3}{i_1}, \ldots, \frac{i_M}{i_1}\right).$$

As the constant $\epsilon$ depends only on position within an image all components of the ratio vector r will be independent of the constant $\epsilon$ and thus independent of the illumination intensity and geometrical factors in the imaged scene.

The invention is applicable to problems in which all histological variation can be described by K parameters. The concept of a parameter vector is introduced and defined as $$p = (p_1, p_2, \ldots, p_K) p \in P$$

where the space P defines all possible parameter variation and thus variation in tissue histology. Using the current invention it is possible to recover a parameter vector from a vector of image ratios. To achieve this it is necessary to have some technique for predicting a vector of image ratios from a given parameter vector. This can be achieved via some experimental technique or with an appropriate mathematical model of light transport within the tissue of interest. Techniques such as Monte Carlo modelling or the Kubelka-Munk approximation have been developed for this purpose. With such a model it is possible to predict a remittance spectrum which corresponds to a unique point in parameter space, that is a unique tissue histology. With a knowledge of the spectral response of the illuminating light source and the spectral response of the filters, used in the image acquisition system, it is possible to predict a vector of image values for a given point in parameter space. This can be expressed as $$r = \langle i_1, i_2, \ldots, i_M \rangle i \in I$$

where the space I defines all possible measurements made by the optical system. Using an appropriate definition of image ratios, such as on the one given above, it is possible to obtain a vector of image ratios. This can be expressed as $$r = \langle r_1, r_2, \ldots, r_N \rangle r \in R$$

where the space R defines all possible image ratios that can be obtained from the space of image measurements. A function $f$ can now be defined which maps from points in parameter space to points in the space of image ratios. To implement this function it is first necessary to compute the spectral reflectance of the material of interest for the given set of parameter values, or point in parameter space. Using this spectral reflectance, along with the spectral responses each of the filters $R^n(\lambda)$, a vector of image values can be calculated. Finally from this a vector of ratios can be obtained. This three-stage mapping can written as $$f : P \rightarrow R$$

to denote the mapping from parameters space to the space of image ratios. Provided that a remittance spectrum can be defined for any possible parameter combination then this mapping is defined for the whole or parameter space. The proposed invention deals with the inverse of this function, defined as $$g : R \rightarrow P$$

which denotes the mapping from the space of image ratios back to parameter space. A key part of the invention is to establish whether a suitable function g can be defined which will allow any measured ratio to be mapped back to the appropriate parameter combination. Such a mapping must be 1-1. That is, for every point in the space of image ratios there must be a corresponding unique point in parameter space. If this is not the case, ambiguity will arise as it could be possible to recover more that one set of parameter values from a given vector of image ratios. To establish this condition, it is first necessary to deal with the function $f$, which must be considered a vector valued function of a vector variable, that is, $$r = f(p).$$

To establish whether this function is 1-1 the determinant of the Jacobian matrix, corresponding to this mapping, can be analysed. This is defined as $$J = \begin{pmatrix} \frac{\partial f_1}{\partial p_1} & \frac{\partial f_1}{\partial p_2} & \cdots & \frac{\partial f_1}{\partial p_K} \\ \vdots & \vdots & \cdots & \vdots \\ \frac{\partial f_N}{\partial p_1} & \frac{\partial f_N}{\partial p_2} & \cdots & \frac{\partial f_N}{\partial p_K} \end{pmatrix} = \begin{pmatrix} \frac{\partial r_1}{\partial p_1} & \frac{\partial r_1}{\partial p_2} & \cdots & \frac{\partial r_1}{\partial p_K} \\ \vdots & \vdots & \cdots & \vdots \\ \frac{\partial r_N}{\partial p_1} & \frac{\partial r_N}{\partial p_2} & \cdots & \frac{\partial r_N}{\partial p_K} \end{pmatrix}.$$

If the determinant of this matrix is non-zero at a point in parameter space then there exists a neighbourhood around this point where the function $f$ can be approximated linearly. This means that any points within this region will map under a 1-1 mapping to a unique point in parameter space. If, when using a system to image a given tissue, it can be established that the Jacobian is non-zero across the whole of parameter space then the function $f$ will be 1-1 everywhere.

Once this condition has been established it is necessary to find either an approximation or an exact analytic expression for the function g which will enable image ratios to be mapped to specific parameters. Although in some cases it may be possible to obtain an analytic function, in most cases it will be necessary to construct a piecewise continuous approximation. This can be achieved by discretising parameter space in suitably small intervals and generating the corresponding image ratio values for every point within a discretised space. Some form of multidimensional interpolation technique, such as a cubic spline, is then used to construct a continuous piecewise approximation to the function g. This then allows processing of pixels from an imaged tissue to give the corresponding set of parameter values. Any number of pixels may be processed in this way to produce a number of parametric maps, which give quantitative information on the parameters of interest across the whole of the imaged scene.

Such maps are of immense value to clinicians and other persons interested in the composition of specific tissues.

The implementation of the proposed invention proceeds along the following steps:
1. For the tissue to be imaged identify all parameters whose variation could cause a change in spectral remittance when illuminated with light.
2. Have, by some means, a method for predicting the spectral remittance of a given tissue for any combination of the identified tissue parameters.
3. Establish the spectral responses of each channel of the given imaging system and from this define an appropriate set of image ratios.
4. Check that the mapping from the space of parameters to the space of image ratios is 1-1 over the range of all parameter variation.

5. If this condition holds obtain some function, either exact or approximate, which maps points in the space of image ratios to the corresponding point in parameter space.

6. Using this function images can then be processed to give quantitative information on the underlying tissue histology.

According to a third aspect of the invention there is provided apparatus for analyzing at least one parameter of a body component, comprising a light source for illuminating the component with light of at least a first and second predetermined waveband, a photoreceptor for receiving light of at least said first and second predetermined wavebands remitted by the component reflected by the surface at a photoreceptor; surface reflection elimination means for eliminating light reflected by the surface of the component, where the predetermined wavebands are chosen such that the component parameter is a one to one function of the ratio between the amount of light remitted by the component of the first predetermined wavebands and the amount of light remitted by the component of the second predetermined waveband, and microprocessor means for analyzing the light received at the photoreceptor to provide a ratio between the light of the first waveband and the light of the second waveband, and from this calculating the component parameter.

The wavebands having image ratios which map 1-1 to a parameter of component vary depending upon the particular component, and the particular parameter to be analysed.

Typically the method and apparatus are used to analyse all the parameters required to characterize a particular component, with the light source and photoreceptor emitting and receiving for each parameter, a pair of wavebands chosen such that the ratio between the amounts of light remitted by the component of each waveband (ie the image ratio for that pair of wavebands) is a 1-1 function of the particular parameter. In practice, the minimum number of wavebands to be monitored will be equal to n+1, where n equals the number of parameters.

It has been found for skin that three parameters characterize the tissue, namely skin thickness, melanin concentration and blood concentration and melanin and blood concentration may be analysed effectively using the methods and apparatus of the invention.

The required predetermined wavebands may be found using the method described above iteratively.

According to a fourth aspect of the invention, there is provided a method of deriving a pair of predetermined wavebands suitable for use in analysing a given parameter of a body component, the method comprising the steps of:

1) defining a set of potential wavebands
2) defining one or more image ratios, the or each image ratio for a region being obtained by dividing the amount of light remitted by the component of a given waveband for that region, the "image value" for that filter, by another image value for that same region;
3) for a component parameter to be analysed and for said defined set of potential wavebands and for said given image ratios, obtaining a function mapping points in parameter space to points in image ratio space;
4) determining whether the mapping function provides a 1:1 correspondence between points in parameter space and points in image ratio space; and
5) if the mapping function does not provide a 1:1 correspondence, rejecting said potential wavebands, repeating steps 1) to 4) and, if the mapping function does provide a 1:1 correspondence accepting the potential wavebands as a candidate set of predetermined wavebands.

The key step in the present invention is that of identifying a set of filter properties and image ratio and a mapping function which maps image ratios to tissue parameters with a 1:1 correspondence. This first step may require consideration of many potential filter properties and corresponding mapping functions.

Preferably, for each filter the method of the present invention is used to determine the centre wavelength of the filter. The method may additionally be used to determine the full width half maximum (FWHM) of the filter characteristic.

Preferably, step 3) comprises constructing a Jacobian matrix for the mapping function with respect to said parameter(s), and obtaining the determinant of that matrix. If the determinant is strictly positive or strictly negative over the entire parameter space, then a 1:1 correspondence between points in parameter space and points in image ratio space is assumed. It will be appreciated that these operations may be performed using multiple processing steps or may be combined into a single processing step.

Embodiments of the present invention may involve the calculation of an error, indicative of the accuracy of parameter recovery obtained using said mapping function. The error may be calculated as follows:

a) calculate the error associated with image acquisition for each vector of each image ratio;
b) from the image ratio vector error, calculate the maximum possible error in each component of the parameter vector across the whole of parameter space; and
c) use the vector of parameter errors at each point within parameter space to measure the accuracy of parameter recovery.

Alternatively corrections may be made for error by standard mathematical error correction algorithms the choice of which will be apparent to the skilled addressee of the specification.

The present invention may be incorporated into many different filter property calculation schemes. For example, in a scheme using a genetic algorithm, the method may be used to identify a plurality of candidate filter parameter sets. The method of the present invention is then applied repeatedly to find an optimal filter parameter set using the candidates.

Alternatively, the method may be employed in a scheme using a gradient descent algorithm. In such a scheme, the method of the third aspect of the present invention is employed to identify a first candidate set of filter parameters. This set is then used to make a selection of another set of filter properties, and the process repeated as often as necessary to arrive at an optimal solution. Of course, any suitable optimization algorithm can be used to compute an optimal solution or a solution which has sufficient accuracy.

Each time the method steps 1) to 4) are carried out, the image ratios may or may not be changed. That is to say that, for each repetition, the potential wavebands and the image ratios may be changed, or only the potential wavebands may be changed.

Although this invention is applicable with particular advantage to the non invasive analyzing of tissue—typically animal and preferably human tissue it will be appreciated that the method and apparatus could also be used to monitor parameters of a material where the parameters characterizing the material have wavelength specific optical properties and where it is possible to control the spectral characteristics of the illumination.

According to a fifth aspect of the invention there is provided a method of determining a property or properties of each of a set of filters, which filters are used to select specific wavelength ranges to quantify a parameter or parameters of a tissue, the method comprising the steps of:

1) defining a set of potential filter properties
2) defining one or more image ratios, the or each image ratio for a region being obtained by dividing the quantified output of a given filter for that region, the "image value" for that filter, by another image value for that same region;
3) for an object or material to be analysed and for said defined set of potential filter properties and for said given image ratio, obtaining a function mapping points in parameter space to points in image ratio space;
4) determining whether the mapping function provides a 1:1 correspondence between points in parameter space and points in image ratio space; and
5) if the mapping function does not provide a 1:1 correspondence, rejecting said potential filter properties, repeating steps 1) to 4) and, if the mapping function does provide a 1:1 correspondence accepting the potential filter properties as a candidate set of filter properties.

According to a sixth aspect of the present invention there is provided apparatus for analysing an object or material having means for conducting a spectral analysis of remitted, emitted, and/or transmitted light to quantify a parameter or parameters of an object or material, the apparatus comprising a plurality of filters for splitting said light into respective components, the filters having properties obtained by using the method of the above first aspect of the invention.

It will be appreciated that the filters of the apparatus may be implemented in optical, electrical electronic, or software form.

BRIEF DESCRIPTION OF THE DRAWINGS

Methods and apparatus according to the various aspects of the invention will now be described, by way of example only with reference to the accompanying drawings, in which.

Figure 1:
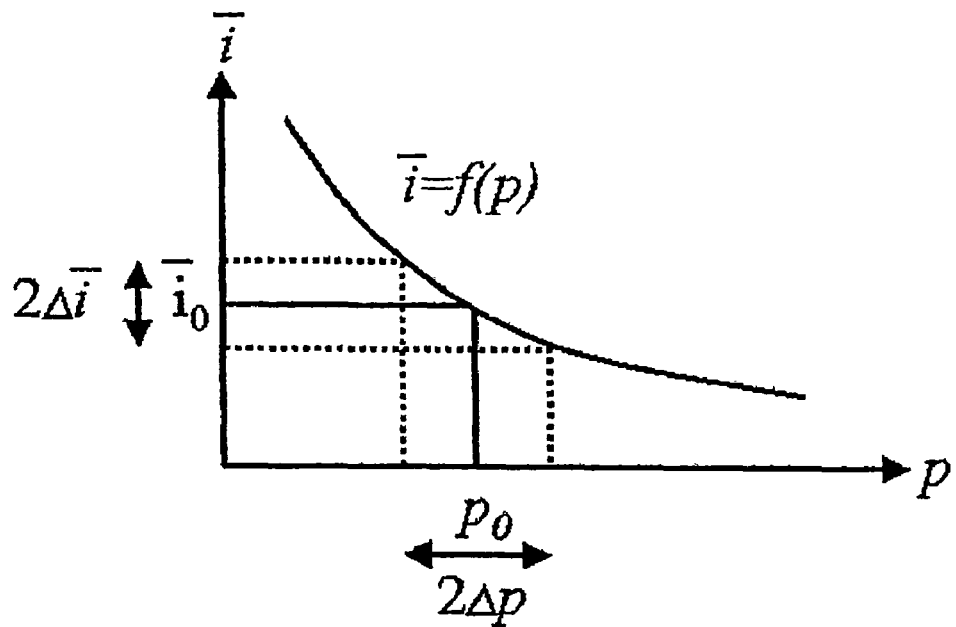
FIG. 1 illustrates a function $f$ which maps an image ratio $\bar{\imath}$ to a material parameter p.
Figure 2:
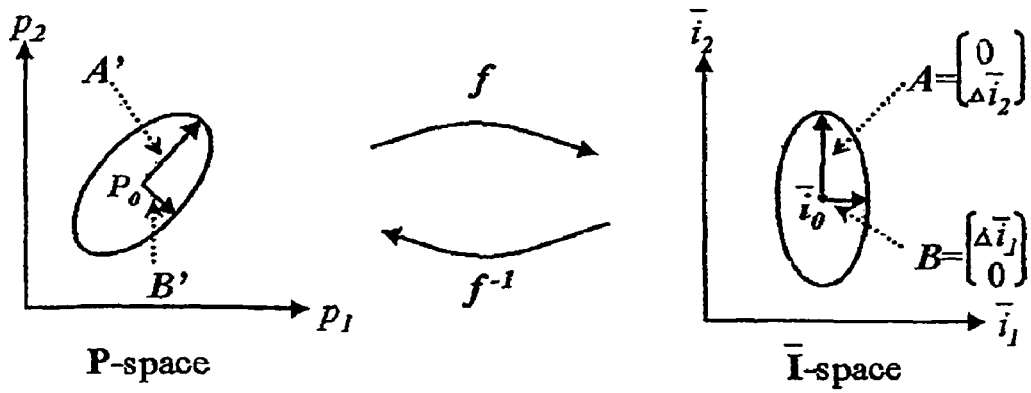
FIG. 2 illustrates a combination of errors in parameter space, mapped to image ratio vector space.

The proof of the theory behind the selection of appropriate wavebands and image ratios for a given parameter will now be described with reference to FIGS. 1, 2 and 6

In a typical analysis system, light remitted from an object can be measured using a digital camera with a small number of optical filters representing a number of wavebands. Image values—brightness or "intensity"—for each image location (x, y) for a given filter (the nth filter) are given by:

$$i^n(x, y) = K_b C_b^n + K_s C_s^n \quad (2)$$

$$= K_b \int E(\lambda) S(\lambda) R^n(\lambda) d\lambda + K_s \int E(\lambda) R^n(\lambda) d\lambda$$

where $K_b$ and $K_s$ are the geometric terms of the body and surface components respectively and $C_b^n$ and $C_s^n$ are colour terms. The first integral in equation (2) is the product of three terms: $E(\lambda)$ is the illuminating light, $S(\lambda)$ is the spectral remittance from the body of the imaged object, and $R^n(\lambda)$ is the spectral response of the nth optical filter. In the second integral there are only two terms as there is no wavelength dependence on the surface component of reflection. The dichromatic reflection model is very important for 3-D scene analysis as it allows for both colour and geometrical analysis of objects within a scene.

A key issue is to show that the technique proposed here is valid for problems where the intensity of the illuminating light is unknown (whilst assuming that the spectral definition of the illuminating light is known). For this purpose the incident light is written as:

$$E(\lambda) = \epsilon_0 E_0(\lambda) \quad (3)$$

where $\epsilon_0$ is a wavelength independent scaling factor. Equation (2) now becomes $$i^n(x,y) = \epsilon \int E_0(\lambda) S(\lambda) R^n(\lambda) d\lambda \quad (4)$$

where $\epsilon = \epsilon_0 K_b$. A digital camera records an N-dimensional vector of image values at each location (x; y). If a mapping, which is independent of the constant $\epsilon$, can be established between the vector of image values and the vector of parameters, then it will be possible to recover scene parameters from image data in a way that does not depend on illumination intensity or scene geometry.

We now introduce the concept of an image ratio, obtained by dividing one image value, calculated from equation (4), by another. For a given image vector, the nth image ratio is given as:

$$\bar{\imath}^n = \frac{i^n}{i^m} \quad n \neq m. \quad (5)$$

Simple consideration of equation (4) shows that any ratio defined in this way will be invariant to a change in the parameter $\epsilon$. Thus any method for the recovery of parameter values from image ratios will be independent of scene geometry and illumination intensity.

The objective here is to extract quantitative parameters upon which the object colouration depends, not to find statistical similarities. Moreover, the specific filters are chosen to maximise the distance in the image ratio space between vectors corresponding to similar parameter values, as this minimises the error on the parameter value recovered from the colour image.

The technique described is generally applicable to scenes in which a small number of parameters are required to describe all possible objects object characteristics. In the formulation, the parameters will be considered to vary continuously. Thus, the technique will be particularly applicable to problems where object characteristics need to be measured across an image. For example a medical imaging system may be required to analyse a particular tissue. The underlying structure of the tissue will not vary, only specific characteristics such as thickness of the different layers (including zero thickness) or the concentration of a particular chemical constituents (including zero concentration). In this situation a small parameter vector can describe all possible variations in the characteristics of the imaged scene. For K scene parameters the parameter vector is defined as:

$$p = \sum_{k=1}^{K} p_k \quad p \in P \tag{6}$$

and the space P defines all potential object characteristics. Ultimately, a mapping from image ratios back to the parameter vector is required, but first the forward problem of obtaining image ratios for a given parameter vector is considered. A reflectance spectrum, corresponding to a given point within parameter space, can be described by the vector in M dimensional wavelength space:

$$\lambda = \sum_{m=1}^{M} \lambda_m \quad \lambda \in \Lambda \tag{7}$$

where the space $\Lambda$ defines all possible spectral reflectance functions. The mapping a, defined as $$a: P \rightarrow \Lambda \tag{8}$$

is introduced to denote the mapping from parameter space to wavelength space. This mapping gives the spectral reflectance of the object specified by the vector p. Such a mapping can be achieved either by a spectroscopic measurement, or by using a mathematical model which takes as input the parameters and produces a corresponding reflectance spectrum. Models of light propagation in different media, such as the Monte Carlo method or the Kubelka Munk approximation, can be used for this purpose. It must be possible to perform this mapping across the whole of parameter space, thus defining every possible spectral reflectance function.

A digital camera with N optical filters records an N-dimensional image vector at each pixel. The image vector is given as:

$$i = \sum_{n=1}^{N} i^n \quad i \in I \tag{9}$$

where I describes the space of all possible image values. The process of image acquisition can be considered as the projection of points in wavelength space to points in filter space. This projection is performed by the mapping function:

$$b: \Lambda \rightarrow I. \tag{10}$$

Equation (4) performs this mapping b in continuous form. In discrete form, the response of the nth optical filter, is given as:

$$i^n = \epsilon \sum_{m=1}^{M} R_m^n \lambda_m \tag{11}$$

where $\lambda_m = E_0(\lambda)S(\lambda)$ and the positive weights at each wavelength are given by $R_m^n$, thus defining each filter response function. A digital camera effectively performs the mapping b, projecting points from a large dimensional space (wavelength space) to a small dimensional space (filter space). With such a mapping there will be a substantial loss of information. However, even with this loss of information, it should be possible to define the mapping in such a way that accurate information regarding the original parameter values can still be recovered from image data. Conditions for this mapping will be discussed in the following later.

Most current image acquisition systems use an RGB system of filters. Although this defines a potential mapping b, it may not be the best mapping with which to recover parameter values from image data. However, it is known to select specific filters to obtain better clarity of data than that possible with an RGB system (although mainly for visualization or image segmentation, not for quantification). Also, in spectrometry, particular spectral wavelengths are selected using statistical methods to improve quantification of components in mixtures. It will therefore be appreciated that an objectively defined set of optical filters is able to perform the task of recovery of parameters, which describe the variation in human skin, better than a standard RGB system.

Once the vector of image values has been obtained, a vector of image ratios can be calculated using equation (5). The vector of image ratios is given as:

$$\bar{i} = \sum_{\bar{n}=1}^{\bar{N}} \bar{i}^{\bar{n}} \quad \bar{i} \in \bar{I} \tag{12}$$

where $\bar{I}$ describes the space of all possible image ratios. The mapping from filter space to the space of image ratios is performed after image acquisition and will be referred to as mapping c, defined as:

$$c: I \rightarrow \bar{I}. \tag{13}$$

There are many ways to define the image ratios and thus the mapping c. For example, pairs of image values could be used to define image ratios as:

$$\bar{i}^n = \frac{i_{2n-1}}{i_{2n}} \quad n = 1, 2, \ldots, \frac{N}{2} \tag{14}$$

or a single image value could be taken as the denominator with which to calculate image ratios from the remaining image values, for example:

$$\bar{i}^n = \frac{i_n}{i_1} \quad n = 2, 3, \ldots, N. \tag{15}$$

At most the dimensionality, $\bar{N}$, of the new space will be one less that that of the original filter space, N. This would correspond to the definition given in equation (15). Alternatively, if the image ratios were defined as given in equation (14), then the dimensionality of the new space will be half that of the original filter space. The aim is to recover a K-dimensional parameter vector from $\bar{N}$ image ratios. Thus there must be at least as many image ratios as parameters, that is, $\bar{N} \geq K$.

The function $f$ defined as:

$$f = a \circ b \circ c \; f: P \rightarrow \bar{I} \tag{16}$$

represents the three stage mapping from parameter space to wavelength space, to image space, and finally to the space of image ratios. For a given set of optical filters, it will be possible to perform this mapping across the whole of parameter space, provided that it is possible to obtain a spectrum for any given parameter vector. The inverse of function $f$ is defined as:

$$f^{-1}: \bar{I} \rightarrow P \tag{17}$$

and maps from the space of image ratios directly to parameter space. If it is possible to define an appropriate $f^{-1}$, it will be possible to recover parameter values from image data in a way that is independent of illumination intensity and scene geometry. The ultimate aim is to find the optimum $f^{-1}$ which maximises the accuracy of parameter recovery. Before a detailed discussion of this mapping is presented, it is important to emphasise that the form of the function $f$ will depend on the mappings a, b and c. Although mapping a is fixed for a given problem, mapping b will vary with the choice of optical filters and mapping c will vary depending on how the image ratios are defined.

Any mapping function which is to map from the space of image ratios ($\bar{I}$-space) to parameter space (P-space) must be 1 to 1. That is, for a given point in P-space, there must be a corresponding unique point in $\bar{I}$-space and vice-versa. If this is not the case, ambiguity will arise as it could be possible to recover more that one set of parameter values from a given vector of image ratios. Once this condition has been established, it is necessary to consider the error associated with parameter recovery as, using a digital camera, it will only be possible to obtain image values to within a given uncertainty. This will introduce an uncertainty into the final recovery of the parameter vector. There could also be an error associated with the prediction measurement of a spectrum from the parameter vector. For simplicity the analysis presented here will be restricted to problems in which the error associated with the spectral measurement can be neglected.

Initially, the problem where one parameter is sufficient to describe all variation in an imaged scene will be analysed. The methodology will then be extended to problems where the number of parameters is greater than one.

Consider the case where one image ratio (two image values) is used to recover a single parameter value. FIG. 1 illustrates a function $f$ which gives the image ratio as a function of the parameter p. It is clear that in order to satisfy the 1 to 1 condition, the curve must not have any turning points: that is, it must increase or decrease monotonically in the appropriate range of p. Mathematically this is expressed as:

$$\left| \frac{df}{dp} \right| > 0 \quad \forall\, p \in P. \tag{18}$$

Measurement of an image ratio value $\bar{i}_0$, corresponding to a parameter value $p_0$, is now considered. Associated with acquisition of each image value is an uncertainty due to camera error. It is straightforward to show, using standard error analysis, that the error associated with an image ratio $\bar{i}$, which has been calculated from the two image values $i_1$ and $i_2$, is given as:

$$\Delta \bar{i} = \Delta i \left( \frac{i_1 + i_2}{i_2^2 - (\Delta i)^2} \right) \tag{19}$$

where $\Delta i$ is the camera uncertainty. This error has been shown on the ordinate of the graph in FIG. 1. If the derivate of $f$ is non-zero in some neighbourhood of $p_0$ then it is possible to approximate this function linearly. Assuming the error $\Delta i$ to lie within this neighbourhood, the corresponding error in the parameter value is given as:

$$\Delta p = \Delta \bar{i} \Big/ \frac{df}{dp}. \tag{20}$$

Thus, it is possible to obtain a value for the error $\Delta p$, associated with parameter recovery, at any point in P-space. An optimisation criterion can then be defined based on some measure of this error. For most applications it will be necessary to minimise the error equally across the whole of P-space. For others it may be that high accuracy parameter recovery is required within a certain range of parameter values. For example, in a medical image application, imaged tissue could be deemed pathological once a characterising parameter changes beyond a threshold level. This would need to be accounted for with some form of weighting in the optimisation criterion. It is interesting to note that in order to minimse $\Delta p$, it is necessary to maximise the magnitude of the derivative given in equation (18). This will ensure that any search, carried out to find an optimum $f$, will tend to move towards regions of search space where the 1 to 1 condition is satisfied.

In theory it is possible to recover the parameter using more than one image ratio. In this case it will be necessary to calculate the error associated with parameter recovery for each of the image ratios and select the one, at each point in P-space, which has the smallest associated error ($\Delta p$). It may be that the optimisation procedure gives a single image ratio which performs better than any other across the whole of P-space. In this situation there is no benefit to using more that one image ratio.

The analysis is now extended to the general problem where the recovery of a K-dimensional parameter vector is required from an $\overline{N}$ dimensional vector of image ratios. Initially the analysis will be restricted to the case where $\overline{N}=K$ and will then be extended to include situations where $\overline{N}>K$. As discussed earlier, if $\overline{N}<K$, then it is not possible to recover K-dimensional data from an $\overline{N}$ dimensional measurement.

The mapping function f, defined as:

$$\bar{i} = f(p) \tag{21}$$

must now be considered a vector valued function of a vector variable. In the following analysis specific results from differential geometry will be used. For further details the reader is directed to for example M. M. Lipschutz, Differential geometry (McGraw-Hill Book Company, New York, 1969). To establish whether the function $f$ provides a 1 to 1 relationship, it is first necessary to consider the behaviour of the determinant of the Jacobian matrix, simply referred to as the Jacobian. This is defined as:

$$\det\left( \frac{\partial f_n}{\partial p_k} \right) = \begin{vmatrix} \frac{\partial f_1}{\partial p_1} & \frac{\partial f_1}{\partial p_2} & \cdots & \frac{\partial f_1}{\partial p_k} \\ \cdots & \cdots & \cdots & \cdots \\ \frac{\partial f_n}{\partial p_1} & \frac{\partial f_n}{\partial p_2} & \cdots & \frac{\partial f_n}{\partial p_k} \end{vmatrix}. \tag{22}$$

The Jacobian can be considered the multidimensional equivalent of the one dimensional derivative given in equation (18). The inverse function theorem states that, if the Jacobian is non-zero at a point $p_0$ in P-space, then there exists a neighbourhood around $p_0$ where the function f can be approximated linearly as $$f(p)=f(p_0)+df(p_0)(p-p_0) \quad (23)$$

where df is the differential of f and is given as:

$$df = \frac{\partial f}{\partial p_1}dp_1 + \frac{\partial f}{\partial p_2}dp_2 + \ldots + \frac{\partial f}{\partial p_k}dp_k. \quad (24)$$

It follows that in this neighbourhood the function f provides a 1 to 1 relationship. Thus, if it is possible to establish that the Jacobian is strictly positive or strictly negative throughout the whole of P-space, the function f will be 1 to 1 everywhere. Once this condition has been established, it is necessary to consider how the error associated with image acquisition maps under $f^{-1}$, to give the corresponding error in parameter recovery. The error associated with each image ratio is calculated using equation (19). The combination of errors maps out a hypervolume in $\bar{I}$-space, centred on the point $i_0$. This has been illustrated in FIG. 2 for the case of a 2D P-space, where an ellipse is obtained (or a circle if the errors are equal). An ellipsoid is obtained in 3D space and a hyperellipse in higher dimensions. Although the following analysis will be based on a 2D P-space, the arguments are equally valid in higher dimensions.

The ellipse in $\bar{I}$-space represents all possible image ratio vectors which could correspond to a camera measurement $\bar{i}=\bar{i}_0$. It is assumed that the region of error lies within the neighbourhood of $\bar{i}=\bar{i}_0$ where the mapping function f can be approximated linearly. Thus, under the mapping $f^{-1}$, the ellipse in $\bar{I}$-space maps directly to another ellipse in P-space. This new ellipse is centred on the point $p=p_0$ and represents all possible parameter vectors which could be recovered from the vector of image ratios $\bar{i}=\bar{i}_o$. The error associated with parameter recovery is obtained by considering the worst case scenario: that is the point within the ellipse in P-space which is at the maximum distance from the point $p=p_0$. This maximum distance must be calculated separately for each component, $p_k$, of the parameter vector to obtain the error associated with recovery of each individual component. To calculate these errors it is necessary to consider how the ellipse is transformed under the mapping $f^{-1}$, which is linear provided the Jacobian is non-zero.

Under a linear mapping the ellipse will be translated, scaled and rotated. The translation associated with the linear mapping defines the point $p=p_0$ which is mapped to from the point $\bar{i}=\bar{i}_0$. The two other transformations, scaling and rotation, are best understood by considering how a vector $d\bar{d}\bar{i}=df$ in $\bar{I}$-space, maps under $f^{-1}$ to give a corresponding vector dp in P-space. The vector dp can be calculated from the inverse form of equation (24) which, in matrix form, is given as:

$$dp = J^{-1}di \quad (25)$$

where J denotes the Jacobian matrix. Note that $J^{-1}$ exists only if the Jacobian in non-zero. This must be the case if the 1 to 1 condition is to be satisfied.

The vectors A and B correspond to the major and minor axes of the ellipse in $\bar{I}$-space and are given as:

$$A = \begin{pmatrix} \Delta \bar{i}_1 \\ 0 \end{pmatrix} \quad B = \begin{pmatrix} 0 \\ \Delta \bar{i}_2 \end{pmatrix}. \quad (26)$$

Under the mapping $f^{-1}$ these vectors map to the vectors A' and B' which correspond to the major and minor axes of the ellipse in parameter space. Solving equation (25) for each of these vectors gives:

$$A' = \begin{pmatrix} \Delta p_1^A \\ \Delta p_2^A \end{pmatrix} \quad B' = \begin{pmatrix} \Delta p_1^B \\ \Delta p_2^B \end{pmatrix} \quad (27)$$

where $\Delta p_1^A$ and $\Delta p_2^A$ are the components of the vector A' in the direction of $p_1$ and $p_2$ respectively. Similarly, $\Delta p_1^B$ and $\Delta p_2^B$ are the components of the vector B' in the direction of $p_1$ and $p_2$ respectively. To calculate the error in each component of the parameter vector it is necessary to consider the worst case scenario. It can be seen from FIG. 2 that this corresponds to taking the maximum of $\Delta p_1^A$ and $\Delta p_2^B$ as the error in $p_1$ and taking the maximum $\Delta p_2^A$ and $\Delta p_2^B$ as the error in $p_2$. This error can be specified by a vector $\Delta p$ and can be calculated for any given point in parameter space. With this measure of the accuracy of parameter recovery across the whole of parameter space, it is possible to define an optimnisation criterion. This could simply be based on a sum of the errors at every point in P-space or could be chosen to favour accuracy of recovery of a subset of the original parameters. Once this optimisation criterion has been defined, a search can be used to find the optimum mapping function f. It is important to note that, although the above discussion is based on a 2D parameter space, the methodology is equally applicable to any K-dimensional parameter space.

An algorithm for the implementation of the proposed methodology is given as follows:

1. Establish a suitable search space from a parameterisation of mappings b and c.
2. For a given mapping function f calculate the vector of image ratios for each point within a discretised parameter space.
3. For each point, check that the Jacobian is either strictly positive or strictly negative across the whole of parameter space. If this condition is held then compute the inverse of the Jacobian matrix. If not then return to step 1 and define a new mapping function f.
4. Using equation (19), calculate the error associated with image acquisition for each vector of image ratios.
5. From the image ratio vector error calculate the maximum possible error in each component, $p_k$, of the parameter vector across the whole of parameter space.
6. Use the vector of parameter errors at each point within parameter space to measure the accuracy of parameter recovery.
7. Repeat steps 2-6 with some optimisation technique which enables an optimum mapping function f to be determined.

It is fairly straightforward to extend this methodology to the case in which $\bar{N}>K$: that is, where there are more image ratios than parameter values. Initially every possible K-dimensional subspace of image ratios will need to be defined from the original $\bar{N}$-dimensional space of image ratios. It will then be necessary to go through the above procedure for each potential subspace and obtain the vector of parameter errors at each point within parameter space. To achieve the maximum possible accuracy the best Δp must be selected at every location within parameter space. Thus every point in P-space will be linked to a specific image ratio combination. It will then be necessary to link every region of the original N̄-dimensional space of image ratios to the particular subspace of image ratios which should be used for parameter recovery. It is important to note that it is necessary to recover the whole parameter vector at each point $\bar{i}_0$ within a particular K-dimensional subspace of image ratios. It is not possible to attempt to improve the accuracy of the system by recovering different components of the parameter vector from different K-dimensional subspaces of image ratios. This is mathematically invalid.

The mapping function f is a composite function of three separate mappings. Although the first mapping a, from parameter space to wavelength space, is fixed for a given problem, mappings b and c can vary depending on the choice of optical filters and definition of image ratios. Thus, to define an appropriate search space it is necessary to parameterise mappings b and c. Mapping b, which represents image acquisition, is defined by the positive N×M matrix $R_m{}^n$, given in equation (11). Typically this matrix will contain many elements and an appropriate parameterisation should be based on typical filter response functions. For example, the position of the central wavelength and a measure of width could be used to define a Gaussian shape.

Parameterisation of the mapping function c will be fairly straightforward as there are only a limited number of ways of combining image values to produce independent image ratios. In some applications the form of this mapping may be fixed apriori. Thus, it will not increase the overall dimensionality of the search space.

An optimisation method should search the whole space of possible mappings using the optimisation criterion outlined in the previous section. One technique which is ideally suited to this type of search is a genetic algorithm, GA, {see T. Back and H. P. Schwefel, "An overview of evolutionary algorithms for parameter optimisation," Evolutionary Computation 1, 1-23 (1993)} as it is straightforward to define a fitness function which measures the accuracy of parameter recovery. Genetic algorithms have been shown to work well on a wide range of problems with objective functions that do not possess "nice" properties such as continuity, differentiability or satisfaction of the Lipschitz Condition {see L. Davis, The handbook of genetic algorithms (Van Nostrand Reingold, New York, 1991), and D. Goldberg, Genetic algorithms in search, optimization and machine learning (Addison-Wesley, London, 1989)}.

The above techniques will now be further exemplified by considering their application to the analysis of a body component, in this case a normal skin composition. Firstly, the prediction of spectral reflectance is considered.

In order to perform mapping a it is necessary to have either a mathematical model which can predict spectral reflectance for a given set of parameter values or some technique for measurement of the appropriate spectrum. For this application we use the mathematical model developed by Cotton and Claridge {see S. D. Cotton and E Claridge, "Developing a predictive model of human skin colouring," Proc. of SPIE Med. Imag. 2708, 814-825 (1996)}. With this model it is possible to predict the spectral reflectance for a given set of parameters. An outline of the model is now given.

Figure 3:
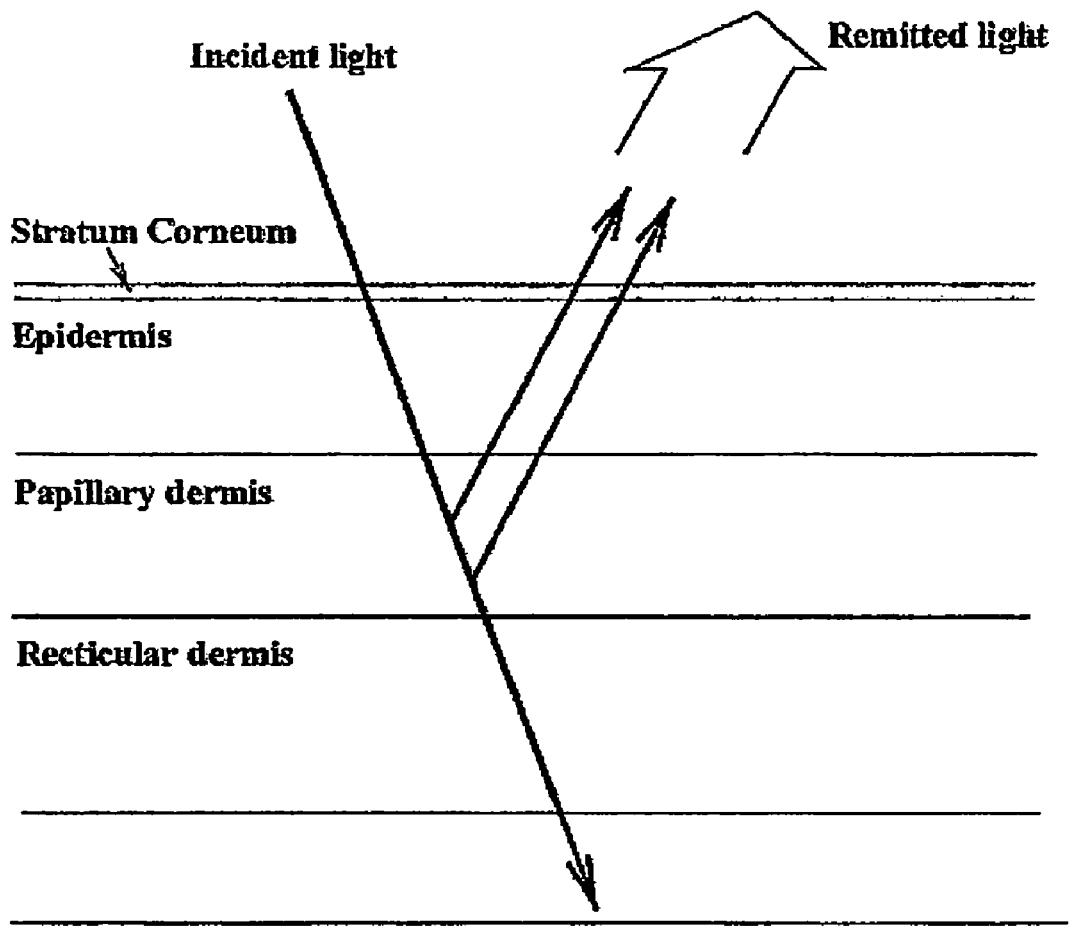
FIG. 3 illustrates a model of the layered structure of skin.

Skin can be considered to be the four-layer structure depicted in FIG. 3. A negligible amount of light is reflected from the surface of the skin, thus the surface term in equation (2) can be neglected. Although not absorbing any radiation, the stratum corneum scatters the incoming light in all directions. Light which penetrates this layer can thus be considered diffuse. In the epidermis light is absorbed by the pigment melanin. The absorption at each wavelength can be calculated using the Lambert-Beer law and will depend on the product of the melanin extinction coefficient and the pigment concentration. After passing through the epidermis the light is both scattered and absorbed by the papillary dermis. The absorption results from the presence of blood and scattering from the underlying collagen structure. The simple Kubelka-Munk light theory {P. Kubelka and F Munk, "Ein Beitrag zur Optik der Farbanstriche", "Z. Tech. Opt" 11, 593-611 (1931)} can be used to model the interaction of light with the papillary dermis as the necessary condition of diffuse incident illumination is satisfied. Any light which passes through the papillary dermis into the recticular dermis can be neglected as no significant backscattering occurs in this layer. Using this two-layer light transport model it is possible to obtain the remitted spectra for given concentrations of melanin and blood. A more detailed description of this model can be found in S. D. Cotton and E Claridge, "Developing a predictive model of human skin colouring", Proc. of SPIE Med. Imag. 2708, 814-825 (1996).

Figure 4A:
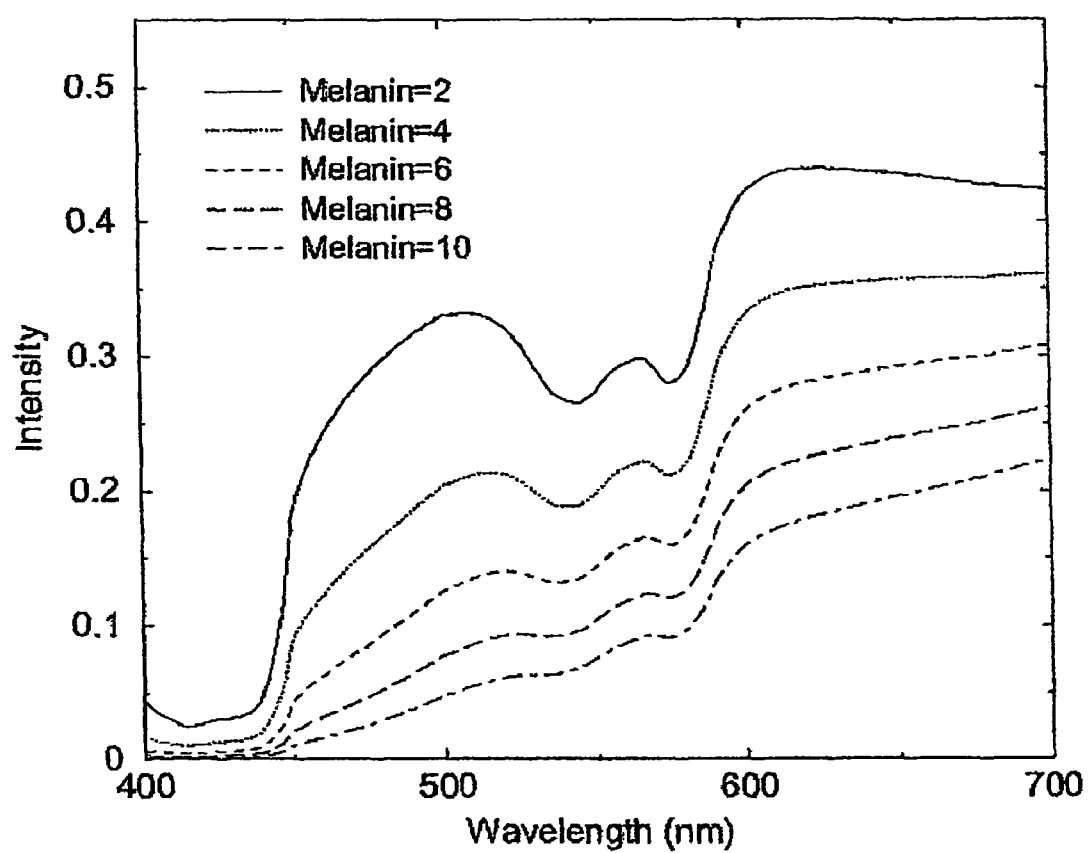
FIGS. 4a and 4b show how the remitted spectrum (intensity vs wavelength) varies for different melanin and blood levels respectively.
Figure 4B:
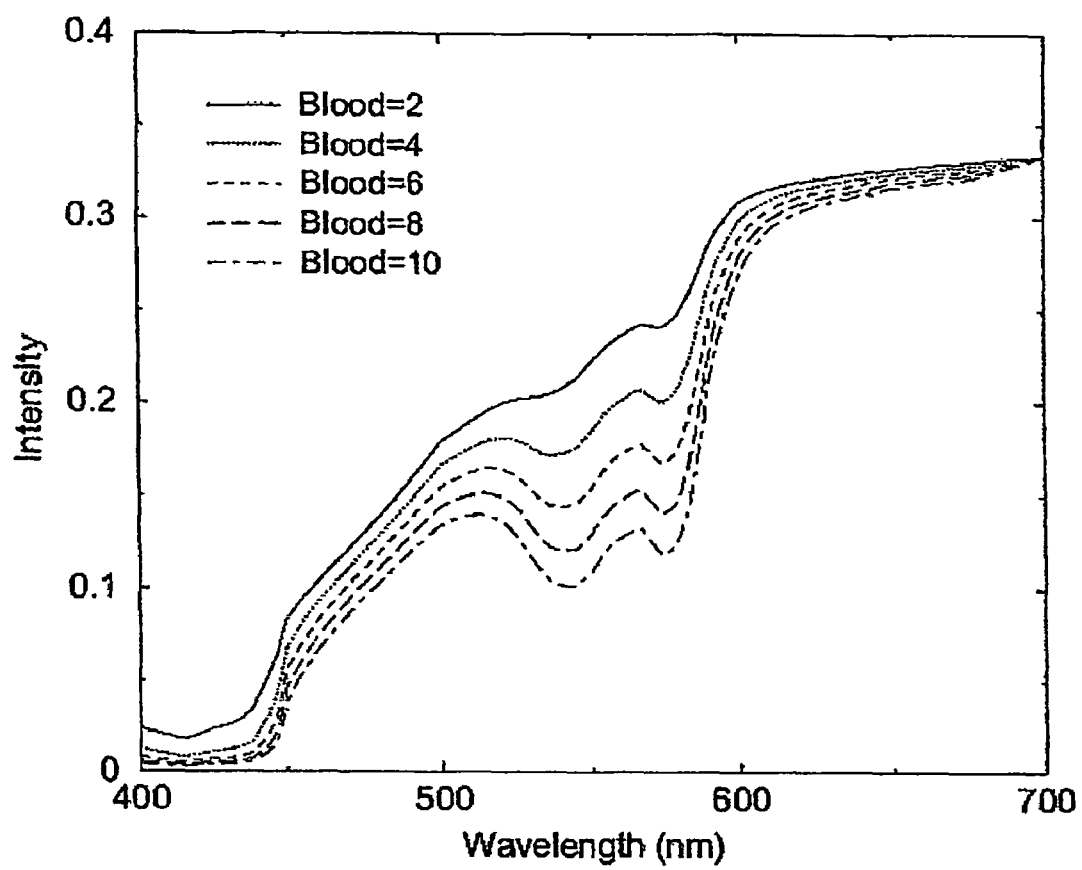

For a given papillary dermal thickness, changes in melanin and blood characterise all histological variation and thus define a 2-D parameter space for healthy skin. To carry out the optimisation procedure described above it is necessary to discretise parameter space. This is done at equal intervals to define 10×10 points, each of which corresponds to a spectrum generated by the mathematical model. For simplicity, concentration values will be denoted by a number between 1 and 10. FIGS. 4a and 4b show how the remitted spectrum changes as melanin and blood are varied respectively. With a change in melanin concentration, the intensity of the whole spectrum is seen to decrease, with a more pronounced change in the blue region. As the blood concentration is decreased the most significant reduction in intensity is observed in the green region, the resulting shape reflecting the two absorption maxima of oxyhaemoglobin, a blood born pigment.

To define a suitable search space it is necessary to parameterise the mappings b and c. A parameterised form of b is chosen to define a typical interference filter. This is modelled as a square profile with Gaussian decay at each side. Two parameters are required to specify this shape: the central wavelength and a full width half maximum (FWHM). Optimisation is carried out for three such filters, defining a 6-D search space. With three filters giving three image values, $i_1$; $i_2$ and $i_3$, the only possible definition of image ratios, if we assume $i_1=i_3$ is equivalent to $i_3=i_1$, is given as:

$$\bar{i}_1 = \frac{i_1}{i_3} \quad \bar{i}_2 = \frac{i_2}{i_3}. \tag{28}$$

In this instance the mapping c does not increase the dimensionality of the search space.

The optimisation procedure was implemented following the algorithm given above. Initially the vector of image ratios was calculated for every point within the discretised parameter space. This was done using the mathematical model to perform mapping a, the parameterised form of matrix $R_n{}^m$ to perform mapping b and the equations (28) to perform mapping c. The derivative of each image ratio, with respect to each parameter, was obtained at each point within discretised parameter space using three-point finite difference approximations. The Jacobian matrix was then constructed at every point within parameter space, and providing its determinant was non-zero everywhere, the inverse calculated. If this condition was violated then a new mapping f was defined. The errors associated with image acquisition were then calculated using equation (19). The absolute value of the error in each image value will vary depending on the camera gain setting. Although this constant will not affect the mapping f, it must be estimated in order to calculate the effective camera error. For this application it was taken to be 0.78% of the maximum value of all the image values across parameter space. This corresponds to a camera which has been set to give a maximum reading for the largest spectral reflectance and a camera error of two grey scale levels in an 8-bit representation.

Using the procedure outlined above the error associated with parameter recovery in both melanin and blood was obtained for each point within the discretised parameter space. In order to find an optimum f, it is necessary to minimise the errors in recovery of both melanin and blood across the whole of parameter space. Thus the fitness function for the GA was taken to be the sum of the errors in both melanin and blood. This procedure was implemented in matlab™ using a standard GA to search the space of available mappings.

The boundaries of the search space were chosen such that the central wavelength was constrained to lie in the visible region (400 nm-700 nm) and such that the widths of the filters were allowed to vary from a FWHM of 25 to 200 nm. Although it is now possible to engineer almost any shape of interference filter, this corresponds to an economically viable range of such filters.

Although it was originally assumed that an image ratio defined as $i_1/i_3$ would be equivalent to $i_3/i_1$, the results of the GA search showed that this was not the case. The search was intitialised for a random seed and, although the same central wavelengths were always obtained, different filters were selected corresponding to $i_3$ defined in equation (28). Further investigation showed that these local maxima in the search space corresponded to differing distributions of errors both, across parameter space and between the two parameters. This is because the fitness function, or measure of accuracy, was defined as the sum the errors across parameter space for both melanin and blood. Thus, a loss of accuracy in one parameter could be compensated for with an increase in the other. It may be that, with a more exact specification of the error distribution in the fitness function, it would be possible to obtain the same results for every GA search.

Figure 5:
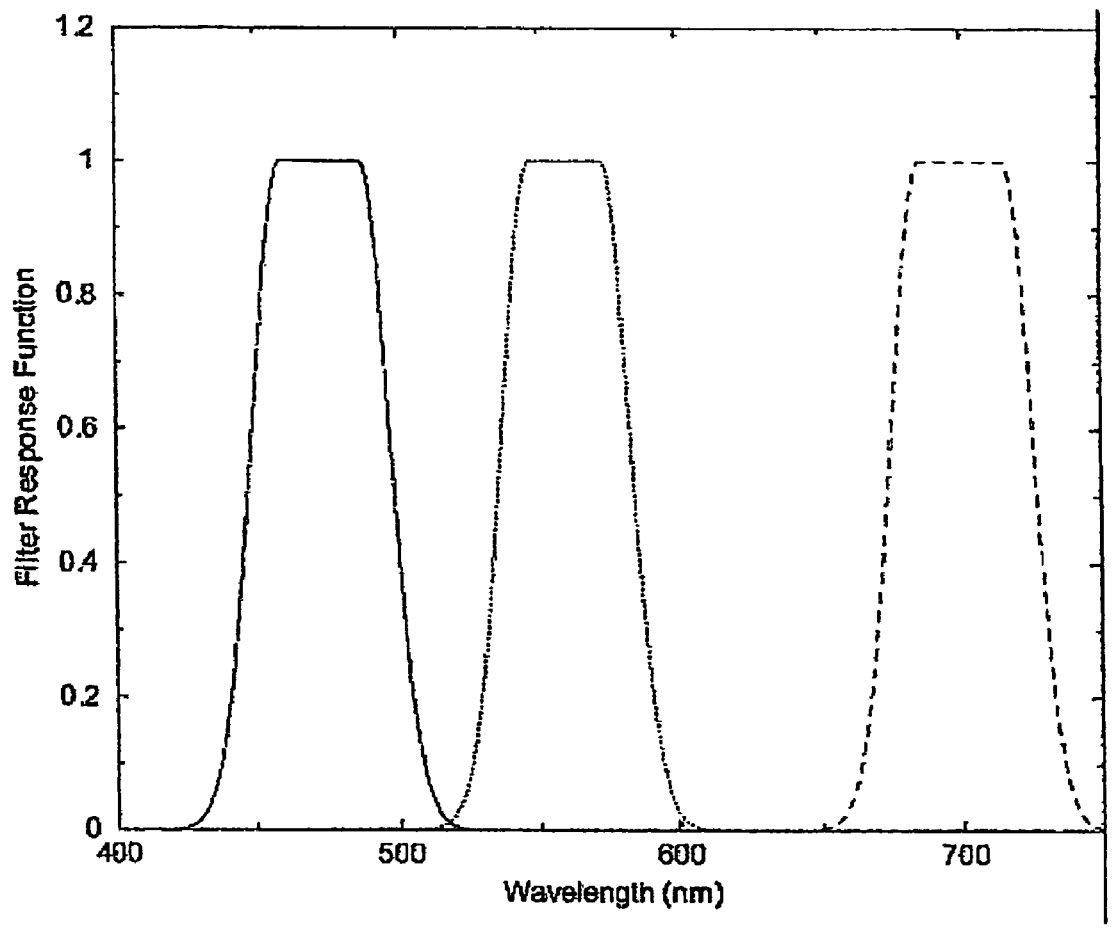
FIG. 5 illustrates a set of filters suitable for analysing blood and melanin levels in skin.

FIG. 5 shows a filter combination which gave a similar error in the recovery of both melanin and blood. The image ratios were calculated by dividing the filter centred at λ=473 nm and λ=560 nm by the response of the filter centred at λ=700 nm. To understand why these specific filters were selected it is necessary to analyse the spectral curves shown in FIG. 4. The filters centred at λ=473 nm and λ=560 nnmm correspond to spectral locations where there is a large change in intensity with the parameters melanin and blood respectively. A third filter was then required in a region of the spectrum in which the remitted light which was either significantly less or significantly more than that of the other two filters. The filter centred at λ=700 nm was chosen as it always gave the largest response at any point within parameter space. This ensured that the derivatives of each image ratio decreased monotonically across the whole of parameter space. The Jacobian, calculated from these derivatives, was strictly positive across the whole of parameter space. It is interesting to note that some alternative filter combinations gave Jacobians which were strictly negative across parameter space, corresponding to alternative local maxima in the search space. If two filters are chosen, to define an image ratio, which vary similarly across parameter space, there will be minimal change in that image ratio and thus it will be of limited value for parameter measurement.

It has been demonstrated that, using an objectively defined set of optical filters, it is possible to recover scene parameters from image data in a way which is insensitive to geometry and incident illumination. In the example problem, discussed above, the error associated with this parameter recovery was found to be relatively small. The invariance of this mapping means that the technique will be particularly applicable to medical image applications where there is significant curvature of the surface of the imaged tissue, such as near a joint. It also means that the method can be used for whole body imaging. It will also be unnecessary to calibrate the camera to determine the intensity of the incident light. This could help to significantly increase the speed of image acquisition and later processing.

The methodology set out here has been developed for a measurement task, where the scene parameters are known to vary continuously. The technique can be also be applied to problems of recognition, where it is necessary to differentiate discrete objects based on some measure of their spectral reflectance. This approach has been discussed in the article G. Healey, "Using colour for geometry-insensitive segmentation," J. Opt. Soc. Am. A 6, 920-937 (1989) who used the idea of normalised colour to identify different regions of normalised colour space corresponding to different metal and dielectric materials. This enabled geometry-insensitive segmentation of an imaged object comprised of a number of different materials.

It will be appreciated that in order to implement the proposed methodology, a look-up table should be established between all possible image ratios and scene parameters. Although this may be time consuming, it is only necessary to carry out this procedure once. Once established, this look-up table will ensure no significant processing after image acquisition, making this technique particularly suitable to real-time applications.

Figure 6:
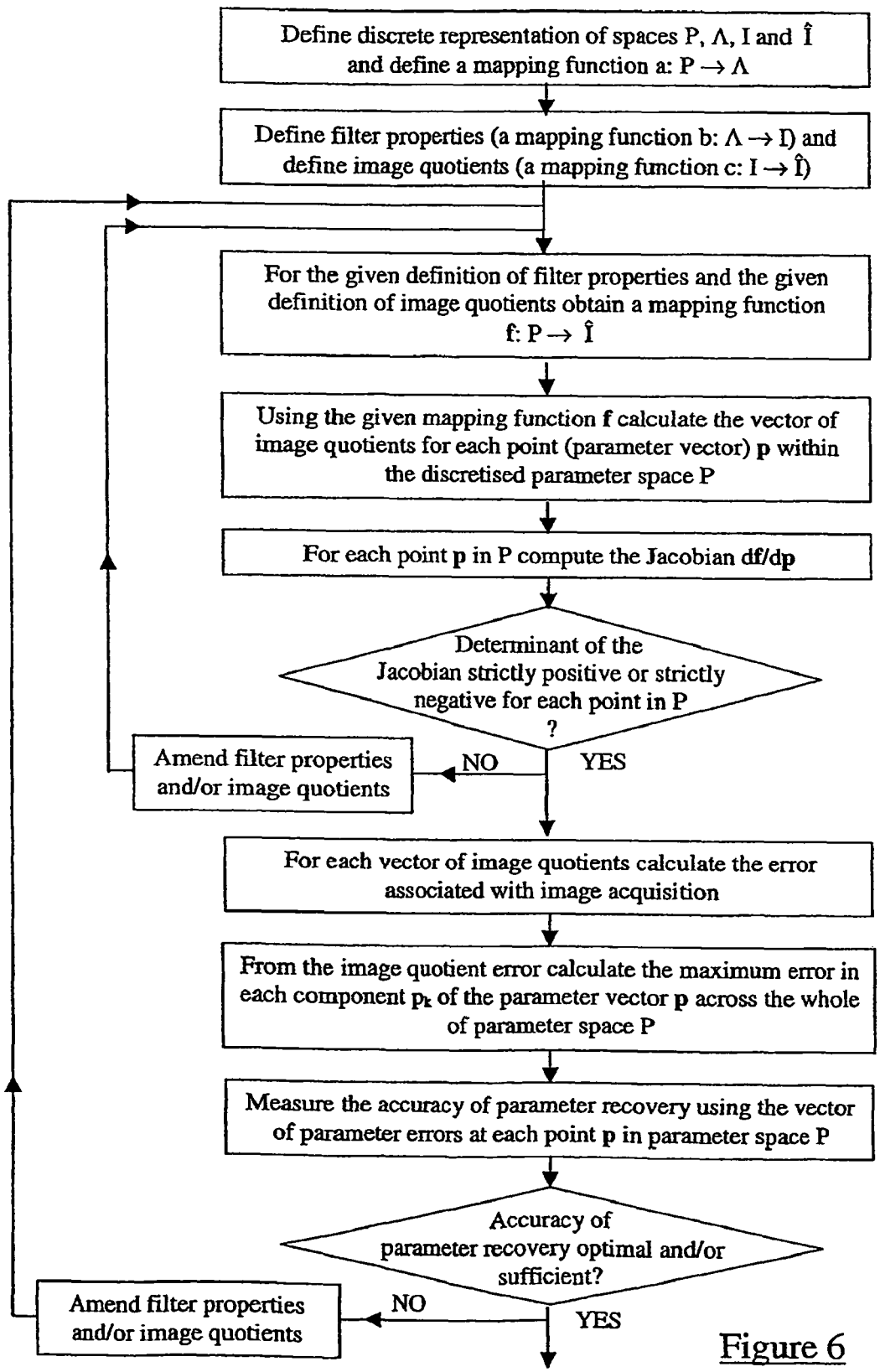
FIG. 6 is a flow diagram illustrating a method of defining a set of filter properties for use in analysing the properties of an object or material.

FIG. 6 is a flow diagram showing the key steps in the method described above.

Figure 8:
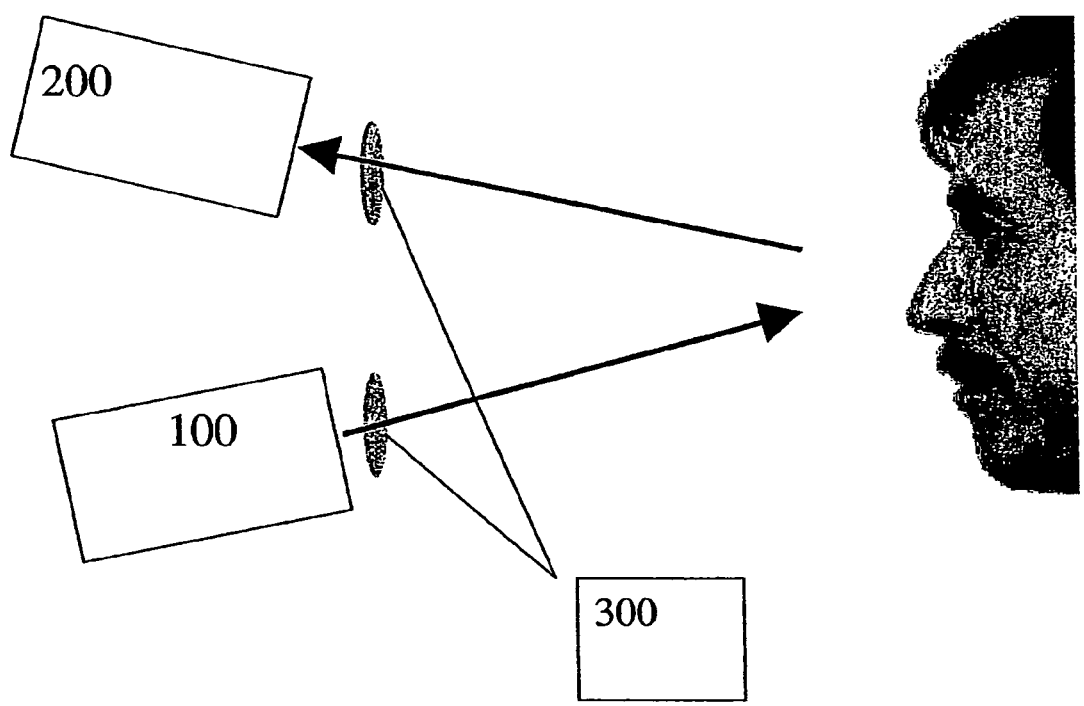
FIG. 8 is a schematic view of a method and apparatus for analyzing facial skin; and, FIGS. 9a, 9b and 9c are respectively, a colour image of a human face taken with a standard digital camera and parametric maps, showing a grey-scale representation of then quantitative measurements of melanin and blood derived using the method and apparatus in accordance with the second and third aspect of the invention.

The method and apparatus for analysing at least one parameter of a body component, in this case animal tissue in the specific form of facial skin is illustrated in FIG. 8. A light source 100 provides illumination to the tissue and remitted light is received at photoreceptor 200 which in this case is a digital camera. Two cross polarised linear polarising filters 300 are used to eliminate the effects of surface reflection from the skin. One filter 300 is placed between the light source 100 and the skin and the other filter 300 is placed between the skin and the digital camera 200.

In this case the digital camera is provided with Red, Green and Blue filters so that light in those wavebands is received by the camera. These wavebands are used-to provide image ratios of which the concentration of melanin and the concentration of blood are one to one function.

The procedure outlined in FIG. 7 was applied to image data in the following way.
1. Two parameters: the concentration of melanin and blood were identified as sufficient to describe all histological variation of healthy tissue.
2. A Kubelka-Munk model of light transport was used to predict the remitted spectrum of tissue for any given combination of melanin and blood concentration.
3. The spectral responses of each of the RGB channels of the colour camera were established and image ratios defined as
   a. Ratio 1=Green/Red Ratio 2=Blue/Red 4. The mapping from the 2-D space of parameter variation to the 2-D space of image ratios was checked to ensure that is was 1-1 across the whole range of appropriate parameter variation.
5. A piecewise continuous approximation was constructed to define a function relating image ratios to histological parameters.
6. Images were acquired using a system of crossed polarising filters, as described above. The experimental set up has been illustrated in FIG. 8.
7. The function described in step 5 was then used to process the image data.
8. Parametric maps were then produced of melanin and blood across the imaged tissue.

Figures 9A, 9B, 9C:
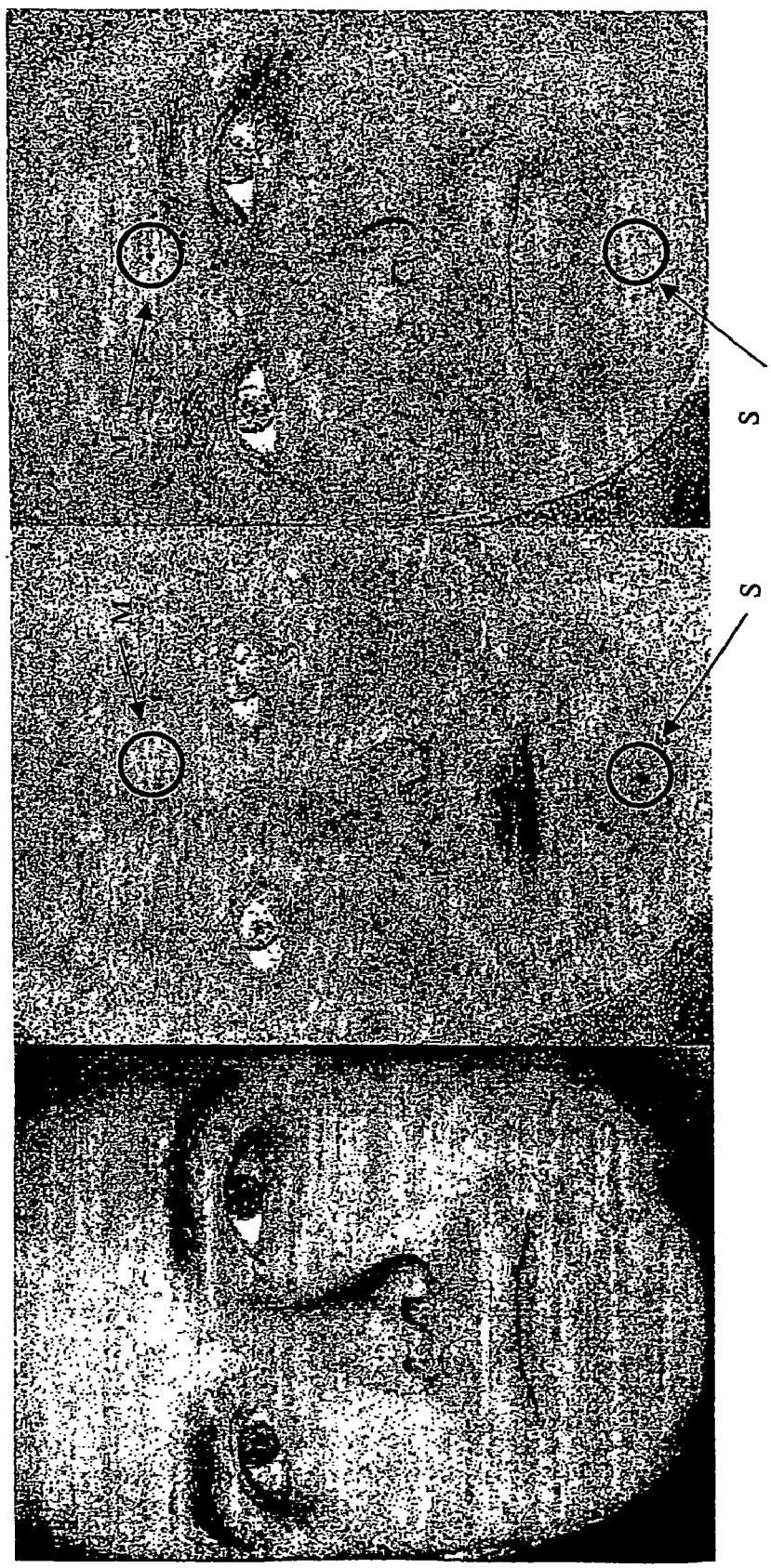

In one experiment this method was applied to an image obtained using a JAI CV-M7CL+ camera imaging facial skin. Parametric maps, showing a grey-scale representation of then quantitative measurements of melanin and blood derived using this technique, are shown in FIG. 9b and 9c.

It should be noted that in 9b illustrating the concentration of hemoglobin concentration across the image, spot S is identified but mole M is not identified. However in 9c illustrating the concentration of melanin across the image, spot S is not identified while mole M is identified. This illustrates simply how useful a tool this can be for a clinician.

A second specific embodiment involves the analysis of images of the human gastrointestinal track obtained using an endoscope. The endoscope system can take two alternative embodiments. In one case the endoscope is equipped with a conventional colour camera and white light source equipped with cross polarizing filters[1]. In a second case the endoscope is equipped with a monochrome camera and a light source equipped with cross polarizing filters[1], with the light source that changes colour sequentially between red, green and blue, and these changes are synchronised with the camera to produce a sequence of red, green and blue images.

[1] one filter being placed between the source of illumination and the component, and the other filter placed between the component and the photoreceptor or photoreceptors with the filters being set at 90 degrees to one another.

Figure 7:
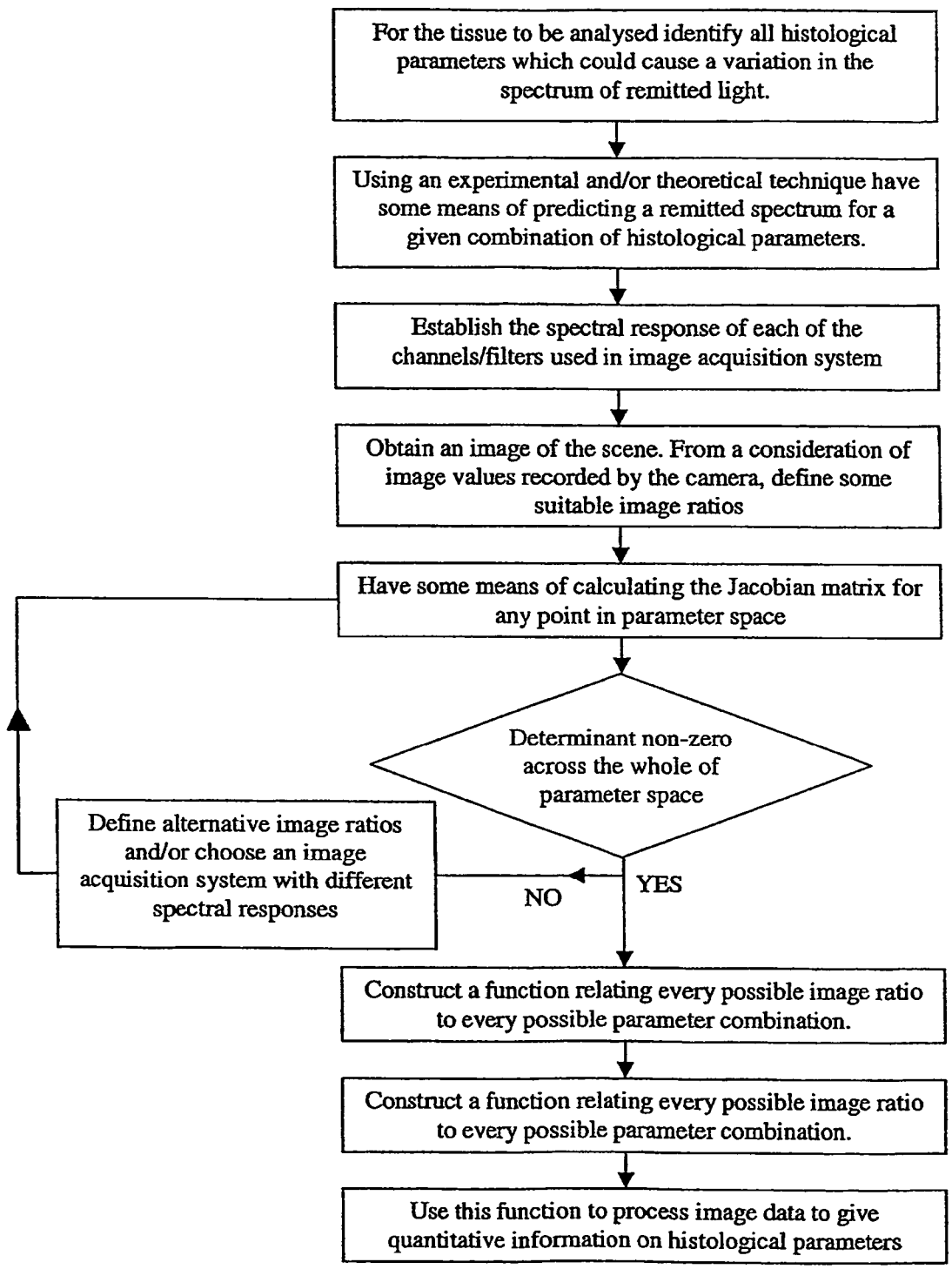
FIG. 7 is a flow diagram illustrating a method of defining a set of suitable wavebands for use in analyzing the parameters of tissue.

The procedure outlined in FIG. 7 is applied to this problem, using data from an endoscope equipped with a conventional colour camera, as follows:
1. Two parameters blood concentration and tissue thickness are identified as sufficient to describe all histological variation.
2. A Monte Carlo model of light transport is used to predict the remitted spectrum of the given tissue for any possible combination of blood concentration and tissue thickness.
3. For an endoscope and camera system, the spectral responses of each of the RGB channels is established and image ratios defined as
    a. Ratio 1=Green/Red Ratio 2=Blue/Red
4. The mapping from the 2-D space of parameter variation to the 2-D space of image ratios is checked to ensure that it is 1-1 across the whole range of appropriate parameter variation.
5. A piecewise continuous approximation is constructed to define a function relating image ratios to histological parameters.
6. Images are acquired the endoscope with a system of crossed polarising filters.
7. The function described in step 5 is then used to process the image data.
8. Parametric maps are then produced to display variation in blood and tissue thickness across the given image.

The procedure can be modified to analyse additional histological parameters with the addition of additional wavebands as described in the equations shown above. These additional wavebands may be obtained by a monochrome camera and light source with cross polarising filters taking a series of images of the subject illuminated by a sequence of coloured lights of known spectral characteristics. The spectral characteristics of one or more of colours may lie outside the visible spectrum

The invention claimed is:

1. An apparatus for determining a distribution of chromophores and/or a thickness of structural layers in a sample of epithelial tissue, the apparatus comprising:
    a polarized light source configured to illuminate said sample of epithelial tissue with polarized light having wavelengths falling within a first, second, and third predetermined wavebands;
    a polarizing filter positioned so as to filter light remitted from said sample of epithelial tissue, said polarizing filter configured to filter out light polarized in a manner generated by said polarized light source;
    an image generator configured to detect filtered remitted light from said sample of epithelial tissue and generate image data indicative of the intensity of filtered remitted light received by said image generator having wavelengths falling within said first, second and third predetermined wavebands;
    a ratio determination module configured to process said image data generated by said image generator to determine for positions within images represented by said image data, a first ratio corresponding to a ratio of light received by said image generator having wavelengths within said second waveband relative to light having wavelengths within said first waveband, and a second ratio corresponding to a ratio of light received by said image generator having wavelengths within said third waveband relative to light having wavelengths within said first waveband;
    a concentration determination module configured to determine for positions within said images represented by said image data by said image generator, concentrations of chromophores and/or the thickness of structural layers of said epithelial tissue at said positions in a sample of epithelial tissue represented by said image data utilizing said first and said second ratios determined for said positions by said ratio determination module; and
    an output module configured to output data representing the determined concentrations of chromophores and/or thickness of structural layers for said positions of said sample of epithelial tissue as determined by said concentration determination module.

2. The apparatus in accordance with claim 1 wherein said image generator comprises a digital camera.

3. The apparatus in accordance with claim 1 wherein said first waveband comprises a waveband corresponding to red light.

4. The apparatus in accordance with claim 1 wherein said second waveband comprises a waveband corresponding to green light.

5. The apparatus in accordance with claim 1 wherein said third waveband comprises a waveband corresponding to blue light.

6. The apparatus in accordance with claim 1 wherein said first waveband comprises a waveband centered on a wavelength of 700 nm.

7. The apparatus in accordance with claim 1 wherein said second waveband comprises a waveband centered on a wavelength of 560 nm.

8. The apparatus in accordance with claim 1 wherein said third waveband comprises a waveband centered on a wavelength of 473 nm.

9. The apparatus in accordance with claim 1 wherein one of said first, second or third wavebands comprises infrared light.

10. The apparatus in accordance with claim 1 wherein said concentration determination module comprises a look up table associating pairs of said first and second ratios generated by said ratio determination module with items of data identifying concentrations of blood and melanin, wherein the blood and melanin when illuminated with polarized light are liable to remit cross polarized light having wavelengths falling within said first, second and third wavebands at said first and second ratios.

11. The apparatus in accordance with claim 10 wherein said pairs of first and second ratios and said concentrations of blood and melanin comprise ratios and concentrations determined by analyzing samples of epithelial tissue.

12. The apparatus in accordance with claim 10 wherein said pairs of first and second ratios and said concentrations of blood and melanin comprise ratios and concentrations determined utilizing a mathematical model of an expected remittance of illuminated light by said samples of epithelial tissue having differing concentrations of blood and melanin.

13. The apparatus in accordance with claim 1 wherein said concentration determination module is configured to determine values representative of concentrations of blood and melanin by applying a predetermined mathematical function to said first and second ratios for said positions as determined by said ratio determination module.

14. The apparatus in accordance with claim 1 wherein said concentration determination module comprises a look up table associating pairs of said first and second ratios generated by said ratio determination module with items of data identifying concentrations of blood and tissue thickness, wherein the blood and tissue thickness when illuminated with polarized light are liable to remit cross polarized light having wavelengths falling within said first, second and third wavebands at said first and second ratios.

15. The apparatus in accordance with claim 14 wherein said pairs of said first and second ratios and said concentrations of blood and tissue thickness comprise ratios and concentrations determined by analyzing said samples of epithelial tissue.

16. The apparatus in accordance with claim 14 wherein said pairs of first and second ratios and said concentrations of blood and melanin comprise ratios and concentrations determined utilizing a mathematical model of an expected remittance of illuminated light by said samples of epithelial tissue having differing concentrations of blood and tissue thickness.

17. The apparatus in accordance with claim 1 wherein said concentration determination module is configured to determine values representative of concentrations of blood and tissue thickness by applying a predetermined mathematical function to said first and second ratios for said positions as determined by said ratio determination module.

18. The apparatus in accordance with claim 1 wherein said polarized light source configured to illuminate said sample of epithelial tissue with polarized light comprises:
 a light source; and
 a polarizing filter arranged to polarize light generated by said light source.

19. The apparatus in accordance with claim 18 wherein said light source is configured to illuminate said sample of epithelial tissue sequentially with light having wavelengths falling within different ones of said first, second and third predetermined wavebands.

* * * * *